United States Patent [19]
Möhler et al.

[11] Patent Number: 6,110,902
[45] Date of Patent: Aug. 29, 2000

[54] METHOD FOR THE INHIBITION OF NEURONAL ACTIVITY LEADING TO A FOCAL EPILEPTIC SEIZURE BY LOCAL DELIVERY OF ADENOSINE

[76] Inventors: Hanns Möhler, Feldguetliweg 186, Feldmeilen, Switzerland, 8706; Detlev Boison, Regensbergstr. 242 b, Zürich, Switzerland, 8050

[21] Appl. No.: 08/881,038

[22] Filed: Jun. 23, 1997

[51] Int. Cl.$^7$ ...................................................... A61K 31/70
[52] U.S. Cl. ........................ 514/46; 424/93.21; 424/418; 435/182; 435/325
[58] Field of Search .................... 514/44, 46; 424/93.21, 424/418; 435/325, 182

[56] References Cited

U.S. PATENT DOCUMENTS

| | | | |
|---|---|---|---|
| 5,573,528 | 11/1996 | Aebischer et al. | 604/891.1 |
| 5,597,827 | 1/1997 | Miller et al. | 514/255 |

FOREIGN PATENT DOCUMENTS

| | | |
|---|---|---|
| 0 232 813 | 8/1987 | European Pat. Off. |
| 0 277 917 | 8/1988 | European Pat. Off. |
| WO 89/09816 | 10/1989 | WIPO |
| WO 91/16903 | 11/1991 | WIPO |
| WO 93/08206 | 4/1993 | WIPO |
| WO 93/23418 | 11/1993 | WIPO |
| WO 94/14832 | 7/1994 | WIPO |
| WO 95/02604 | 1/1995 | WIPO |
| WO 95/07921 | 3/1995 | WIPO |
| WO 95/29680 | 11/1995 | WIPO |
| WO 95/30683 | 11/1995 | WIPO |

OTHER PUBLICATIONS

Löscher et al., "Which Animal Models Should Be Used in the Search for New Antiepileptic Drugs? A Proposal Based on Experimental and Clinical Considerations," *Epilepsy Research*, 2, 145–181 (1988).

Lothman et al., "Screening and Characterization of Antiepileptic Drugs with Rapidly Recurring Hippocampal Seizures in Rats," *Epilepsy Research*, 2, 367–379 (1988).

White, "Clinical Significance of Animial Seizure Models and Mechanism of Action Studies of Potential Antiepileptic Drugs," *Epilepsia*, 38(Suppl. 1), S9–S17 (1997).

Zurn et al., "Symptomatic Cell Therapies: Cells as Biological Minipumps," *European Neurology*, 36, 405–408 (1996).

Thomas et al. (eds.), *Taber's Cyclopedic Medical Dictionary*, 17th Edition/Illustrated, F. A. Davis Co., Philadelphia, PA, 1993, only pp. 660–662 supplied, see especially definition of epilepsy at p. 660, column 2.

Berkow et al. (eds.), a portion of Chapter 121 ("Seizure Disorders") in *The Merck Manual of Diagnosis and Therapy*, 16th Edition, Merck & Co. Rahway, NJ, 1992, only pp. 1436–1444 supplied.

Gomaa, "Characteristics of Analgesia Induced by Adenosine Triphosphate," *Pharmacology & Toxicology*, 61, 199–202 (1987).

Adami et al., 1995, Effects of repeated administration of selective adenosine $A_1$ and $A_{2A}$ receptor agonists on pentylenetetrazole–induced convulsions in the rat, Eur. J. Pharmacol. 294:383–389.

Aebischer et al., 1994, Transplantation in Humans of Encapsulated Xenogeneic Cells Without Immunosupression, Transplant 58:1275–1277 (Dec. 1994).

Aebischer et al., 1991, Long–Term Cross–Species Brain Transplantation of a Polymer–Encapsulated Dopamine–Secreting Cell Line, Exp. Neurol. 111, 269–275.

Aebishcer et al., 1994, Functional Recovery in Hemiparkinsonian Primates Transplanted with Polymer–Encapsulated PC12 Cells, Exp. Neurol. 126:151–158.

Barone et al., 1989, Adenosine Receptor Prodrugs: Towards Kidney–Selective Dialkylxanthines, J. Pharmacol. Exp. Ther. 250:79–85 (Issue No. 1).

Chin, 1989, Adenosine Receptors in Brain: Neuromodulation and Role in Epilepsy, Ann. Neurol. 26:695–698 (Issue No. 6, Dec. 1989).

Collis and Hourani, 1993, Adenosine receptor subtypes, TIPS 14, 360–366 (Oct. 1993).

Concas et al., 1996, Differential Antagonism by the Selective $A_1$ Adenosine Receptor Agonist CCPA of Seizures Induced by NMDA, Kainic Acid, and Domoic Acid, Neuroscience Research Communications 18:9–18 (Issue No. 1).

Corradetti et al., 1984, Adenosine Decreases Aspartate and Glutamate Release from Rat Hippocampal Slices, Eur. J. Pharmacol. 104:19–26.

Cottam et al., 1993, New Adenosine Kinase Inhibitors with Oral Antiinflammatory Activity: Synthesis and Biological Evaluation, J. Med. Chem. 36, 3424–3430 (Issue No. 22).

De Sarro et al., 1991, Anticonvulsant action of 2–chloroadenosine infected focally into the inferior colliculus and substantia nigra, European Journal of Pharmacology 194:145–152.

Dragunow, 1988, Purinergic Mechanisms in Epilepsy, Progr. Neurobiol. 31:85–108.

Dunwiddie and Worth, 1982, Sedative and Anticonvulsant Effects of Adenosine Analogs in Mouse and Rat[1], J. Pharmacol. Exp. Therap. 220:70–76.

Fisher et al., 1991, Survival and Function of Intrastriatally Grafted Primary Fibroblasts Genetically Modified to Produce L–Dopa, Neuron 6:371–380 (Mar. 1991).

Fisher and Gage, 1994, Intracerebral transplantation: basic and clinical applications to the neostriatum, FASEB J. 8:489–496 (May 1994).

Foster et al., 1994, Regulation of Endogenous Adenosine Levels in the CNS: Potential for Therapy in Stroke, Epilepsy and Pain, Adv. Exp. Med. Biol. 370:427–430.

Franklin et al., 1988, Adenosine receptor activation blocks seizures induced by bicuculline methiodide in the rat prepiriform cortex, European Journal of Pharmacology 150:207–209.

(List continued on next page.)

Primary Examiner—Gary Geist
Assistant Examiner—L. Eric Crane
Attorney, Agent, or Firm—Pennie & Edmonds LLP

[57] ABSTRACT

The present invention relates to the treatment of conditions associated with neuronal activity. Specifically, the invention is drawn to methods and compositions for administering adenosine to inhibit pain syndromes or epilepsy in a patient.

7 Claims, No Drawings

OTHER PUBLICATIONS

Fredholm 1995, Adenosine Receptors in the Central Nervous System, NIPS 10:122–128, (Jun. 1995).

Gossen and Bujard, 1992, Tight control of gene expression in mammalian cells by tetracycline–responsive promoters, Proc. Natl. Acad. Sci. USA 89:5547–5551 (Jun. 1992).

Gossen et al., 1995, Transcriptional Activation by Tetracyclines in Mammalian Cells, Science 268:1766–1769 (Jun. 23, 1995).

Greene and Haas, 1991, The Electrophysiology of Adenosine in the Mammalian Central Nervous System, Progr. Neurobiol. 36:;329–341.

Guieu et al., 1996, Adenosine and the Nervous System: Clinical Implications, Clinical Neuropharmacology 19:459–474 (Issue No. 6).

Herberg et al., 1993, Effect of an Adenosine $A^1$ Agonist Injected Into Substantia Nigra on Kindling of Epileptic Seizures and Convulsion Duration, Pharmacol. Biochem. Behav. 44:113–117.

Jiao et al., 1993, Long–term correction of rat model of Parkinson's disease by gene therapy, Nature 362:450–453 (Apr. 1, 1993).

Maillard et al., 1994, Adenosine Receptor Prodrugs: Synthesis and Biological Activity of Derivatives of Potent, $A_1$–Selective Agonists, J. Pharm. Sci. 83:46–53 (Issue #1, Jan. 1994).

Maitre et al., 1974, Protective Effect of Adenosine and Nicotinamide Against Audiogenic Seizure, Biochemical Pharmacology 23:2807–2816.

McNally et al., 1997, Cloning and Expression of the Adenosine Kinase Gene from Rat and Human Tissue, Biochem. Biophys. Res. Comm. 231:645–650 (Issue No. 3).

Nellen and Lichtenstein, 1993, What makes an mRNA anti–sense–itive, TIBS 18:419–423 (Nov. 1993).

Palmer and Stiles, 1995, Review: Neurotransmitter Receptors VII:Adenosine Receptors, Neuropharmacology 34:683–94 (Issue No. 7).

Petersen, 1991, Selective protection by adenosine receptor agonists against DMCM–induced seizures, European Journal of Pharmacology 195:261–265.

Pospisil et al., 1993, Noradrenaline Reduces Cardiovascular Effects of the Combined Dipyridamole and AMP Administration but Preserves Radioprotective Effects of these Drugs on Hematopoiesis in Mice, Physiol. Res. 42:333–340.

Sabate et al., 1995, Transplantation to the rat brain of human neural progenitors that were genetically modified using adenoviruses, Nature Genetics 9:256–260 (Mar. 1995).

Sagen et al., (Jun.) 1993, Transplants of Immunologically Isolated Xenogeneic Chromaffin Cells Provide a Long–Term Source of Pain–reducing Neuroactive Substances, J. Neurosci. 13:2415–2423 (No. 6).

Sagot et al., 1995, Polymer Encapsulated Cell Lines Genetically Engineered to Release Ciliary Neurotrophic Factor Can Slow Down Progressive Motor Neuronopathy in the Mouse, Eur. J. Neurosci. 7:1313–1322.

Sawynok and Sweeney, 1989, The Role of Purines in Nociception, Neuroscience 32:557–569(No. 3).

Singh et al., 1996, Cloning and characterzation of cDNA for adenosine kinase from mammalian (Chinese hamster, mouse, human and rat) species; High frequency mutants of Chinese hamster ovary cells involve structural alterations in the gene, Eur. J. Biochem. 241:564–571.

Spychala et al., 1996, Cloning of human adenosine kinase cDNA: Sequence similarity to microbial ribokinases and fructokinases, Proc. Nat. Acad. Sci. USA 93:1232–1237 (Feb. 1996).

Suhr and Gage, 1993, Gene Therapy for Neurologic Disease, Arch. Neurol. 50:1252–1258 (Nov. 1993).

Tai and Sun, 1993, Microencapsulation of recombinant cells: a new delivery system for gene therapy, FASEB J. 7:1061–1069 (Aug. 1993).

Thompson et al., 1993, Presynaptic inhibition in the hippocampus, TINS 16:222–227 (Issue No. 6).

Ulrich and Huguenard, 1995, Purinergic Inhibition of GABA and Glutamate Release in the Thalamus: Implications for Thalamic Network Activity, Neuron 15:909–918 (Oct. 1995).

Valerio et al., 1985, Adenosine deaminase: characterization and expression of a gene with a remarkable promoter, EMBO J. 4:437–433 (Issue No. 2).

Voits and Frey, 1994, Stimulation–Dependent Effect of Antiepileptic Drugs in Amygdala Kindled Rats on Both Seizure Score and Duration of Afterdischarges, Pharmacol. Toxicol. 75:54–61.

Von Lubitz et al., 1994, Chronic adenosine $A_1$ receptor agonist and antagonist: effect on receptor density and N–methyl–D–aspartate induced seizures in mice, Eur. J. Pharmacol. 253:95–99.

Winn et al., 1994, Polymer–encapsulated cells genetically modified to secrete human nerve growth factor promote the survival of axotomized septal cholinergic neurons, Proc. Natl. Acad. Sci. USA 91:2324–2328 (Mar. 1994).

Winn et al., 1989, An Encapsulated Dopamine–Releasing Polymer Alleviates Experimental Parkinsonism in Rats, Exp. Neurol. 105:244–250.

Wu and Saggau, 1994, Adenosine Inhibits Evoked Synaptic Transmission Primarily by Reducing Presynaptic Calcium Influx in Area CA1 of Hippocampus, Neuron 12:1139–1148 (May 1994).

Zhang et al., 1994, Activation of adenosine $A_1$ receptors underlies anticonvulsant effect of CGS21680, European Journal of Pharmacology 255:239–243.

METHOD FOR THE INHIBITION OF NEURONAL ACTIVITY LEADING TO A FOCAL EPILEPTIC SEIZURE BY LOCAL DELIVERY OF ADENOSINE

1. FIELD OF THE INVENTION

The present invention relates to the treatment of conditions associated with neuronal activity. Specifically, the invention is drawn to methods and compositions for administering adenosine to inhibit pain syndromes or epilepsy in a patient.

2. BACKGROUND TO THE INVENTION

Epilepsy is a frequent neurological disorder with a lifetime prevalence of about 2 to 5% that manifests itself in varied forms of epileptic seizures. These seizures range from brief lapses of attention (absence seizures) to limited motor, sensory or psychological changes (partial seizures) to prolonged losses of consciousness with convulsive motor activity (idiopathic or symptomatic generalized tonic clonic seizures). Such symptoms are due to synchronous discharges of large populations of neurons based on a deficit in inhibitory neurotransmission or an excess of excitatory neurotransmission. Current drug therapy cannot completely suppress seizure occurrence in approximately 60% of patients (McNamara, 1994, J. Neurosci. 14:3413–3425). Additionally, therapy is often accompanied by adverse drug effects. Drug resistant forms of epilepsy (most of them mesial temporal lobe epilepsies) require resective surgery of the epileptogenic focus. For many patients, this kind of intervention is a final option that carries an inherent risk of morbidity. Even after surgery, most epileptic patients continue to require antiepileptic drug medication for many years.

Treatment of acute and chronic pain is another serious and unresolved medical problem. In patients with chronic pain, the pain signals are transmitted from the site of pain generation by afferent neurons to the spinal cord. These afferent neurons transmit signal to higher centers in the brain which, upon activation, perceive the pain signal. Frequently, patients with pain syndromes such as neuropathic pain and carcinoma-induced pain do not respond to opiate analgesic drugs and hence their symptoms cannot be treated satisfactorily. Accordingly, millions of patients experience intractable pain.

One compound that has been speculated to be useful for as a drug for inhibiting epileptic activity and pain is adenosine. Adenosine is an endogenous compound with known chemical structure. It occurs naturally in low concentrations in nearly all cells of the body but is normally not released except in some pathological conditions. When adenosine is applied in pharmacological doses to various organ systems in vitro it exerts multiple effects by acting on adenosine receptors (Al and A2). Relatively low systemic doses of adenosine receptor agonists produce marked sedation and hypothermia. At high doses, cessation of spontaneous motor activity as well as some ataxia results. Dunwiddie and Worth, 1982, J. Pharmacol. Exp. Therap. 220:70–76.

In brain tissue in vitro, application of adenosine strongly inhibits neuronal activity (Guieu et al., 1996, Clinical Neuropharmacology 19, 459–474). Neuronal excitation is specifically and potently decreased by adenosine inhibiting the release of excitatory neurotransmitters such as glutamate in a presynaptic, calcium dependent mechanism. Thomson et al., 1993, TINS 16:222–227; Wu and Saggau, 1994, Neuron 12:1139–1148. This effect is mediated via activation of the adenosine $A_1$-receptors. Fredholm, 1995, NIPS 10:122–128.

A number of investigators have shown that adenosine and adenosine receptor agonists provide an acute protective effect against epileptic seizures (reviewed in Chin, 1989, Ann. Neurol. 26:695–698; Dragunow, 1988, Progr. Neurobiol. 31:85–108; Foster et al., 1994, Adv. Exp. Med. Biol. 370:427–430; and Greene and Haas, 1991, Progr. Neurobiol. 36:329–341). For example, local microinjection of the adenosine $A_1$-receptor agonist cyclohexyladenosine into the brain reduced the duration of convulsions in a kindling model of epileptic seizures. Herberg et al., 1993, Pharmacol. Biochem. Behav. 44:113–117. However, the drug effect was transient and only observed for a time window of 48–72 hours after injection. Many other investigators have found a similar transient effect inhibiting seizure activity after injection of adenosine receptor agonists.

Conversely, long term administration of the adenosine Al analogue CPA i.p. for 9 days actually increased the incidence of chemically-induced seizures precipitated 2 days after termination of CPA injections. Von Lubitz et al., 1994, Eur. J. Pharmacol. 253:95–99. Similarly, Adami and colleagues found that repeated administration of the adenosine Al receptor agonist CCPA resulted in a marked diminution over time of its anticonvulsant effectiveness in a pentylenetetrazole-model of convulsions. Such a reduction in effectiveness was not observed, however, with repeated administration of adenosine $A_1/A_2$ receptor agonist NECA, or the adenosine $A_2$ receptor agonist 2HE-NECA. Adami et al., 1995, Eur. J. Pharmacol. 294:383–389. Since lethal doses of pentylenetetrazole were used by Adami et al., it is unclear whether the lack of tolerance observed during chronic treatment with adenosine $A_2$ receptor ligands would be maintained in other models of epilepsy.

Adenosine also exerts a powerful antinociceptive action via prejunctional adenosine-receptors in the spinal cord. It has been speculated that adenosine inhibits pain-transducing neurotransmitter signalling. Foster et al., 1994, Adv. Exp. Med. Bio. 370:427–430. In addition, administration of adenosine into peripheral nerve plexus (e.g. plexus axillaris or plexus femoralis) may also inhibit pain. However, adenosine can also induce pain when administered systemically. Presumably, this effect is due to the activation of P2X purinoceptors in the periphery. Sawynok and Sweeney, 1989, Neuroscience 32:557–569.

Accordingly, although transient experiments with adenosine receptor analogs demonstrated a protective effect against seizure activity, long term administration of adenosine receptor agonists may not inhibit seizure activity. Additionally, adenosine receptor agonists exhibited marked adverse effects on the cardiovascular system when administered systemically.

3. SUMMARY OF THE INVENTION

The invention provides a novel therapeutic strategy for the treatment of epilepsies and chronic pain syndromes. In one aspect, the invention provides a method of inhibiting epilepsy or chronic pain in a patient by delivering a chronic local dose of adenosine to a site of neuronal activity involved in the epilepsy or pain in a human patient. The chronic local dose of adenosine can be delivered to the site of neuronal activity by, for example, implantation of an adenosine-releasing polymer or an adenosine-releasing cell. Alternatively, cells at the site of neuronal activity can be induced to produce adenosine.

In another aspect of the invention, there is provided a method of generating a conditionally immortalized adenosine-releasing cell. In particular embodiments, such a method comprises generating a non-human animal embryo having an ADA (−/−) tsA58 (+/−) genotype, or an adenosine kinase (−/−) tsA58 (+/−) genotype, and isolating conditionally immortalized adenosine-releasing cells from the embryo. Alternatively and in another embodiment of the invention, such conditionally immortalized adenosine-releasing cells are derived from patients with severe combined immunodeficiency disease (SCID). Yet another aspect of the invention are conditionally immortalized adenosine-releasing cells.

The invention also provides, in still another aspect, a kit for use in inhibiting pain syndromes or epilepsy in a patient comprising adenosine, adenosine kinase inhibitors, or an adenosine releasing cell, along with a polymer or encapsidation agent.

4. BRIEF DESCRIPTION OF THE FIGURES

FIG. 1. Diagram of a capsule used for intracerebral grafting of ADA-deficient fibroblasts. An example of a therapeutically active capsule is shown, containing $2 \times 10^5$ adenosine releasing fibroblasts. One capsule releases 230 pmol adenosine per day.

FIG. 2. Antiepileptic effect of adenosine released from encapsulated cells in the kindling model of rats. EEG-recordings one day before (top) and 14 days after (bottom) the intraventricular implantation of a capsule containing adenosine releasing ADA-Immorto fibroblasts. Before implantation a very strong afterdischarge (top) following a test stimulus was recorded in both channels (electrodes in hippocampus). After implantation no afterdischarges were observed after the test stimulus (bottom).

FIG. 3. Antiepileptic effect of adenosine released from a synthetic polymer in the kindling model of rats. The effectiveness of adenosine released from a synthetic polymer was tested in the kindling model of epilepsy. Fully kindled rats (day 0) showed a high prevalence of seizures which were graded according to severity (grade 5=highest severity). Following implantation (arrow) the severity of seizures following the test stimulus was drastically reduced (day 1). The antiseizure activity of the implant was apparent for at least 1 week (day 3 and day 7). When the rats were tested 2 weeks after implantation, the protective effect of adenosine was no longer apparent (day 14) since the adenosine supply was exhausted.

5. DETAILED DESCRIPTION OF THE INVENTION

The present invention provides for the use of adenosine to inhibit neuronal activity for therapeutic purposes. In particular, the invention provides for the chronic release of adenosine in therapeutically desired target areas for the treatment of epilepsy and pain syndromes in a human patient. As used herein the term "subject" includes mammals. The term "patient", unless otherwise specified, is understood to mean human patients. Adenosine is released locally in the sites of neuronal hyperactivity in order to control epilepsy, or into the sites of nociceptive regulation in order to inhibit or reduce pain.

5.1. Delivery of a chronic local dose of adenosine

Adenosine, when given orally or systemically, exerts strong side effects affecting all organs which contain adenosine receptors. In particular cardiovascular side effects are prominent and preclude the use of adenosine as a systemic therapeutic agent. However, local application of adenosine into therapeutic target areas exhibits the therapeutic potential of adenosine in the particular target area. Additionally, the biological half life of adenosine is such that adenosine applied locally is not distributed throughout the entire body. Thus, local delivery of adenosine exhibits therapeutic effects without involving the side effects associated with systemic administration. As shown below by way of actual working examples, local delivery of adenosine is therapeutically effective and relatively free of side effects.

For purposes of the invention, the term adenosine preferably includes not only the chemical commonly referred to as adenosine, but also other known adenosine receptor agonists. For example, adenosine analogs are also useful in the methods and compositions of the invention. Currently available effective adenosine analogues are: R/S-PIA=$N^6$-(2-phenylisopropyl)adenosine, CHA=$N^6$-cyclohexyladenosine, CPA=$N^6$-cyclopentyladenosine, CCPA=2-chlorocyclopentyladenosine, Cl936=$N^6$-diphenylethyladenosine, NECA=5'-(N-ethylcarboxamido) adenosine, 2CADO=2-chloroadenosine, CV1808=2-phenylaminoadenosine, CGS21680=2[p-(2-carbonyl-ethyl) phenylethylamino]-5'-N-ethylcarboxamidoadenosine (Collis and Hourani, 1993, TIPS 14, 360–366; Fredholm, 1995, NIPS 10, 122–128; Palmer and Stiles, 1995, Neuropharmacology 34, 683–94). Adenosine agonists include adenosine prodrugs well known in the art such as AMP, AMP in conjunction with dipyridamole, and N-AcADAC. See, for example, Maillard et al., 1994, J. Pharm. Sci. 83:46–53; Barone et al., 1989, J. Pharmacol. Exp. Ther. 250:79–85; and Pospisil et al., 1993, Physiol. Res. 42:333–340. Further, adenosine agonists yet to be discovered are also included within the scope of the invention. Particularly preferred are those adenosine receptor agonists with a short half life in the body, or those which remain localized.

Local levels of adenosine can also be elevated through other mechanisms. Adenosine kinase inhibitors released from an implanted polymer will increase adenosine levels by local inhibition of adenosine kinase. Such adenosine kinase inhibitors include iodotubercidin and derivatives thereof, and inhibitors yet to be discovered. Cottam et al., 1993, J. Med. Chem. 36, 3424–3430.

As used herein, the term "chronic administration" is defined as administering a single dose or implant in such a manner as to cause a locally confined release of drug that is sustained over a period of at least one day, and preferably several days and up to a week or longer (e.g. several weeks or months). In contrast, acute administration of a drug results in a single release of drug at the time of administration.

5.2. Carrier Systems for local delivery

The invention encompasses any method of local chronic delivery of adenosine to a site controlling neuronal activity. Different ways of delivering adenosine to target areas described in more detail below are: adenosine-releasing cells as carriers; adenosine-releasing polymers as carriers; adenosine kinase inhibitor-releasing polymers; and gene therapy vectors for the local endogenous production of adenosine. However, it is also anticipated that other methods of delivering chronic local doses of adenosine may be developed and are within the scope of the invention.

5.2.1. Polymers

Adenosine can be formulated as a slow release implantation device for extended and sustained administration of adenosine. Adenosine is integrated into a suitable polymer (synthetic, natural, biodegradable). The resulting adenosine-containing polymer is a device that can be implanted and will release adenosine by diffusion. Devices that release adenosine at a constant rate over an extended period of time are particularly useful. Polymers have the additional advantage that ligands of adenosine receptors other than adenosine can be included in such polymers and exploited therapeutically. Such chemical agents include various structural analogues of adenosine. Several known structural analogues are described above. Additionally, polymers may be used to deliver a sustained release of adenosine kinase inhibitors or antisense oligonucleotides, as described more fully infra.

Examples of such sustained release formulations include composites of bio-compatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems", Vol. 45 of "Drugs and the Pharmaceutical Sciences", M. Dekker, New York, 1990, and U.S. Pat. No. 5,573,528 to Aebischer et al. (issued Nov. 12, 1996).

For example, ethylene vinyl acetate is dissolved in methylene chloride (10% w/v), the adenosine or adenosine kinase inhibitor is added in the desired concentration and the resulting emulsion is then shock-frozen, lyophilized and extruded into tubes at 50° C. Polymer-based approaches for adenosine delivery, and their therapeutic effectiveness is further described below by way of actual working examples.

5.2.2. Cells

Adenosine can be delivered locally via cells bioengineered to release adenosine. For longterm chronic delivery of the therapeutic substance with the capability of regulated release, adenosine-releasing cells are the method of choice.

Such adenosine-releasing cells can be of exogenous origin. By the term "exogenous" is meant cells obtained from sources other than the subject in which they are implanted for treatment. Exogenous cells can be from other organisms of the same species (such as human-derived cells for use in a human patient). Exogenous cells can also be from heterologous sources, i.e., from a species distinct from the subject to be therapeutically treated (such as mouse cells for use in a human). Encapsidation of compounds and cells is described generally in U.S. Pat. No. 5,573,528. The bioengineering and encapsulation of adenosine-releasing cells is detailed below by way of working examples.

When xenogeneic cells are used for transplantation, encapsidation of the cells into semipermeable polymer membranes provides a number of advantages. For example, the cells are immunologically isolated and therefore have an extended in vivo viability. Additionally, encapsidated cells can be more easily removed from a subject. The grafting of polymer-encapsidated cells has been developed by Aebischer et al., 1991, supra, and has been successfully used with both non-human primates and humans (Aebischer et al., 1994, supra).

Generally, cells are encapsidated by first embedding them into a matrix of either collagen, agarose or PVA (polyvinylacetate). Subsequently, the embedded cells are injected into hollow fibers made of polypropylene of a 60:40 copolymer of polyacrylnitrile:polyvinylchloride. The fibers are cut into pieces and end-sealed.

Apart from exogenous sources, cells can also be taken from the subject or patient. After harvesting, the cells are genetically modified to become adenosine-releasing cells and are then reimplanted. Since the cells are isogeneic, no immune response is to be expected. Therefore encapsulation is not required. Adenosine-releasing cells may also be derived from patients or subjects with severe combined immunodeficiency (SCID) in which the adenosine deaminase (ADA) gene is defective.

Preferably, the adenosine-releasing cells are immortalized by one of several methods. For example and not by way of limitation, cells can be conditionally immortalized. The tsA 58-system described herein below is one method of conditionally immortalizing cells providing the added advantage that the cells grow well in tissue culture at reduced temperatures, yet discontinue division once implanted into a patient and maintained at 37° C. In addition to conditional immortalization, adenosine-releasing cells can be constitutively immortalized by methods well known in the art. Examples of constitutive immortalization methods are transfection with constructs expressing large T antigen, or immortalization by Epstein Barr virus.

Adenosine-releasing cells can be delivered into the target area by at least two procedures of grafting. The cells are embedded in a synthetic or natural polymer, e.g. polymer scaffolds or alginate. Alternatively, the cells are not embedded, but injected directly into the target area. The latter procedure has previously been used for dopamine-releasing cells in the therapy of Parkinson's disease (Fisher and Gage, 1994, FASEB J. 8, 489–496).

Genetically engineered cells have been successfully grafted into the brain of rodents and non-human primates (Suhr and Gage, 1993, Arch. Neurol. 50:1252–1258) and into human nervous tissue (Aebischer et al., 1994, Transplant 58:1275–1277). Further, positive results have been obtained with grafts which included adrenal chromaffine cells releasing analgesic compounds (Sagen et al., 1993, J. Neurosci. 13:2415–2423), PC12 cells releasing dopamine with a survival and release time of more than 6 months (Aebischer et al., 1991, Exp. Neurol. 111, 269–275, and Aebischer et al., 1994, Exp. Neurol. 126:151–158), primary cells such as neuronal precursor cells (Sabate et al., 1995, Nature Genetics 9:256–260), fibroblasts (Fisher et al., 1991, Neuron 6:371–380) and myoblasts engineered to release DOPA or NGF (Jiao et al., 1993, Nature 362:450–453). In addition, cell lines such as BHK (baby hamster kidney) engineered to release CNTF or NGF have been successfully grafted and been active for at least 6 months (Sagot et al., 1995, Eur. J. Neurosci. 7:1313–1322, and Winn et al., 1994, Proc. Natl. Acad. Sci. USA 91:2324–2328).

5.2.3. Ex vivo and in vivo Gene Therapy To Generate Adenosine-Releasing Cells

In order to achieve the release of adenosine from a cell, a high content of adenosine inside the cell has to be generated. This result is achieved by interfering with the adenosine degrading enzymes, adenosine-deaminase and adeno-sine-kinase. These enzymes can either be totally inactivated by gene targeting or they can be downregulated by antisense strategies. Down regulation of the adenosine kinase gene is believed to be most effective at generating cells that release adenosine. Alternatively, adenosine levels in the cell may be increased by providing the rate-limiting substrates or enzymes for its synthesis.

A knock-out of either of the two adenosine degrading enzymes adenosine kinase and/or adenosine deaminase or of both enzymes will lead to an accumulation and release of adenosine. The genes can be knocked out directly in suitable cell lines. Alternatively, adenosine releasing cells can be derived from mice which contain a knock-out mutation of either one or both of the adenosine-degrading enzymes. An example of the generation of adenosine releasing fibroblasts from such knock-out mice is described below in the Examples section.

Expression of the adenosine degrading enzymes adenosine deaminase and adenosine kinase is downregulated by the expression of corresponding antisense RNAs. Nellen and Lichtenstein, 1993, TIBS 18:419–423. For example, vectors which express antisense RNAs for adenosine kinase and/or adenosine deaminase are introduced into cells (endogenous cells, tissue culture cells or mouse oocytes from which transgenic mice are generated as cell donors) in order to downregulate expression of the endogenous genes. Cells are thereby generated which release adenosine. As a refinement of this procedure, regulatable promoter systems (Gossen and Bujard, 1992; Gossen et al., 1995) for antisense expression can be used which permit adenosine release to be controlled by promoter-regulating agents. Alternatively, an antisense-releasing polymer may be implanted into the subject, whereby the polymer releases antisense polynucleotides that are taken up by target cells in the implantation site. In this manner, cells adjacent to the antisense-releasing polymer are induced to release adenosine.

Antisense approaches involve the design of oligonucleotides (either DNA or RNA) that are complementary to the target mRNA. Both the adenosine kinase gene and the adenosine deaminase gene have been cloned from humans and other mammals. See Valerio et al., 1985, EMBO J. 4:437–433; Spychala et al., 1996, Proc. Nat. Acad. Sci. USA 93:1232–1237; Singh et al., 1996, Eur. J. Biochem. 241:564–571; McNally et al., 1997, Biochem. Biophys. Res. Comm. 231:645–650. The antisense oligonucleotides will bind to the complementary target mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non-translated, non-coding regions of the target gene transcripts could be used in an antisense approach to inhibit translation of endogenous adenosine deaminase and/or adenosine kinase. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of the target mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. These studies should utilize controls that distinguish between antisense gene inhibition and nonspecific biological effects of oligonucleotides. It is also preferred that these studies compare levels of the target RNA or protein with that of an internal control RNA or protein.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988), or hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

The antisense molecules should be delivered to cells that express high levels of adenosine deaminase or adenosine kinase in vivo, e.g., cells of neuronal and non-neuronal origin such as neuronal precursor cells and fibroblasts. A number of methods have been developed for delivering antisense DNA or RNA to cells; e.g., antisense molecules can be injected directly into the tissue or cell derivation site, implanted in an antisense-releasing polymer, or modified antisense molecules, designed to target the desired cells (e.g., antisense linked to peptides or antibodies that specifically bind receptors or antigens expressed on the target cell surface) can be administered.

Another antisense inhibition approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous target transcripts and thereby prevent translation of adenosine deaminase and/or adenosine kinase mRNA.

For example, a vector can be introduced in vivo such that it is taken up by a cell and directs the transcription of an antisense RNA. Such a vector can remain episomal or become chromosomally integrated, as long as it can be transcribed to produce the desired antisense RNA. Vectors can be plasmid, viral, or others known in the art, used for replication and expression in mammalian cells. Expression constructs may be inserted into the appropriate cells within a subject using vectors which include, but are not limited to adenovirus, adeno-associated virus, retrovirus and herpes virus vectors, in addition to other particles that introduce DNA into cells, such as liposomes.

Expression of the sequence encoding the antisense RNA can be by any promoter known in the art to act in mammalian, preferably human cells. Such promoters can be inducible or constitutive. These promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the target site; e.g., the brain. Alternatively, viral vectors can be used which selectively infect the desired tissue or cell type; (e.g., viruses which infect neural cells).

Ribozyme molecules designed to catalytically cleave adenosine deaminase and/or adenosine kinase RNA transcripts can also be used to prevent translation of target mRNA and expression of their protein products. (See, e.g., PCT International Publication WO90/11364, published Oct. 4, 1990; Sarver et al., 1990, Science 247:1222–1225). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. Construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of adenosine deaminase and/or adenosine kinase. Preferably the ribozyme is engineered so that the cleavage recognition site is located near the 5' end of the target mRNA; i.e., to increase efficiency and minimize the intracellular accumulation of non-functional mRNA transcripts.

Ribozymes for use in the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug et al., 1984, Science, 224:574–578; Zaug and Cech, 1986, Science, 231:470–475; Zaug et al., 1986, Nature, 324:429–433; published International Patent Application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in adenosine deaminase and/or adenosine kinase mRNA sequences.

As in the antisense approach, the ribozymes can be composed of modified oligonucleotides (e.g. for improved stability, targeting, etc.) and should be delivered to cells which express target mRNAs in vivo, e.g., neural or glial cells. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

Alternatively, endogenous adenosine deaminase and/or adenosine kinase gene expression can be reduced by targeting deoxyribonucleotide sequences complementary to the regulatory region of the respective genes (i.e., the promoter and/or enhancers) to form triple helical structures that prevent transcription of the target gene in target cells in the body. (See generally, Helene, C. 1991, Anticancer Drug Des., 6(6):569–84; Helene, C. et al., 1992, Ann, N.Y. Acad. Sci., 660:27–36; and Maher, L. J., 1992, Bioassays 14(12):807–15).

5.2.4 Animal Models For In vivo Testing Of Therapeutic Methods

A number of different animal models of epilepsy are available for testing therapeutic effectiveness. These include chemical, electrical and audiogenic induced seizures. Examples of chemical convulsants are pentylenetetrazol (PTZ) (Speckmann and Caspers, 1973, Epilepsia 14:397–408), strychnine (Johnson, 1978, Ann. Rev. Pharm. Tox. 18:269–289), kainic acid (Johnson et al., 1974, Nature 248:804–805), PTX (Johnson, 1978, supra), 3MP (Lamar, 1970, J. Neurochem. 17:165–170) and biculline methiodide (BMI) (Franklin et al., 1988, Eur. J. Pharm. 150:207–209), to name just a few. Other chemical convulsants are well known to those of skill. Mice that are genetically sensitive to audiogenic seizures (Swiss albino mice of the RB strain)

are available from the Laboratoire de Physiologie Acoustique (Jouy-en-Josas, France).

However, the preferred model for epilepsy is the kindling test. In this animal model, epilepsy is induced by progressive electrical stimulation of the animal subject's brain. The kindling test is the classical standard test for the evaluation of anticonvulsant agents for two reasons. The kindled animal represents the most widely accepted model of the pathophysiology underlying human partial and generalized epilepsy. In addition, all classical anticonvulsant agents that are presently in clinical use are effective in the kindling test. Voits and Frey, 1994, Pharmacol. Toxicol. 75:54–61 and Lothman et al., 1988, Epilepsy Res. 2:367–369.

Several different animal models of pain syndromes have been developed and are well known in the art. These include the hot plate test and the tail flick test for acute pain (D'Amour and Smith, 1941, J. Pharm. Exp. Ther. 72:74–79) and the formalin test for chronic rheumatic pain (Du Buisson and Dennis, 1977, Pain 4:161–174). In addition, nerve ligations are used as models of neuropathic pain, in particular the model of Bennett, 1993, Muscle and Nerve 16:1040–1048. Bennett's model is also relevant for abnormal evoked pain such as allodynia and hyperalgesia. Since an analgesic effect for adenosine can be expected only after local application, cells or polymers releasing adenosine will be administered intrathecally or epidurally in the spinal cord or into peripheral nerve plexus. Yaksh and Rudy, 1976, Phys. Behav. 17:1031–1036.

5.3. Indications, Dosages and Formulation

The methods and compositions of the invention are indicated for all forms of epilepsies, and are especially advantageous in the treatment of temporal lobe epilepsy. The invention will also find use in the treatment of the following epileptic syndromes.

1) Focal epilepsies:
Including idiopathic epilepsies such as benign childhood epilepsy with centrotemporal spikes, childhood epilepsy with occipital paroxysms or primary reading epilepsy, symptomatic epilepsies with simple partial seizures, complex partial seizures, or secondarily generalized seizures;

2) Generalized epilepsies and syndromes:
Including idiopathic epilepsies such as benign neonatal familial convulsions, benign neonatal convulsions, benign myoclonic epilepsy in infancy, childhood absence epilepsy, juvenile absence epilepsy, juvenile myoclonic epilepsy, epilepsy with grand mal seizures on awakening; Cryptogenic or symptomatic epilepsies such as West syndrome, Lennox-Gestaut syndrome, epilepsy with myoclonic-astatic seizures, epilepsy with myoclonic absences, and Symptomatic epilepsy such as early myoclonic encephalopathy or specific syndromes;

3) Epilepsies with undetermined origin such as neonatal seizures, severe myoclonic epilepsy in infancy, epilepsy with continuous spike and wave EEG during slow-wave sleep, acquired epileptic aphasia (Landau-Kleffner syndrome); and 4) Special syndromes which are situation related such as febrile convulsions, isolated seizures or isolated status epilepticus, or seizures arising after an acute metabolic or toxic event, and post traumatic epilepsies.

Epilepsy can be diagnosed by clinical, electrographical and brain-imaging criteria. The methods of the invention provide an added advantage in that they may be used for treatment of patients suffering from epilepsies that do not respond satisfactorily to presently available antiepileptic drugs or do not tolerate the side effects associated with these drugs.

The present invention is also useful to ameliorate all forms of acute and chronic pain, in particular carcinoma-induced pain, neurogenic pain, postoperative pain, neuropathic pain, and neuralgic pain. Specific pain syndromes that may be treated with the methods and compositions of the invention include pain associated with soft tissue disease and peripheral damage (e.g. acute trauma, osteoarthritis, rheumatoid arthritis, burns, episiotomy), spinal pain, musculo-skeletal pain, upper-extremity pain, myofascial pain syndromes, headache, deep and visceral pain syndromes (e.g. heart pain, muscle pain, eye pain, orofacial pain, abdominal pain, gynecological pain and pain during labour), pain associated with nerve and root damage (e.g., peripheral nerve disorders or infections, amputation-induced pain, peripheral neuropathies, tic douloureux and atypical facial pain, arachnoiditis), carcinoma-induced pain (particularly that involving bone and soft tissue carcinoma and metastases), and central nervous system-induced pain (such as central pain due to spinal cord or brain stem damage). Many patients with chronic pain or carcinoma pain do not respond to opiates, and can be successfully treated with the methods and compositions of the invention.

In order to supply a local chronic dose of adenosine to treat epilepsies, adenosine-releasing cells or polymers are stereotactically implanted into or near the epileptogenic focus. For treatment of chronic pain syndromes, implantation of adenosine releasing polymers, cells or encapsidated cells is done intrathecally or epidurally to block pain transmission in spinal cord. Alternatively, adenosine releasing polymer, cells or encapsidated cells can be implanted into a peripheral nerve plexus e.g. plexus axillaris or plexus femoralis that is involved in pain transmission in the pain syndrome. For all indications, dosages can be altered by, for example, varying the size of the implant, using different cell numbers or compound concentrations in the implant, and by using different polymers with different biodegradation rates.

The therapeutic dosing and regimen most appropriate for patient treatment will of course vary with the disease or condition to be treated, and according to the patient's weight and other parameters. The results presented hereinbelow demonstrate that a dose of adenosine equivalent to about 250 ng/adenosine/day (or less, see below) administered constantly over several days up to two weeks can ameliorate epileptic symptoms. It is expected that much smaller doses, e.g., in the 25 ng/adenosine/day range, and longer duration of treatment, will also produce therapeutically useful results, i.e., a statistically significant decrease in epileptic events or severity. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of adenosine normally produced by nerve cells which is on the order of 0.03 to 0.3 $\mu$M (extracellular concentration) in the resting state, rising to 30 to 300 $\mu$M after nerve cell stimulation (Corradetti et al., 1984, Eur. J. Pharmacol. 104:19–26; Fredholm, 1995, NIPS 10:122–128; and Aulrich and Huguenard, 1995, Neuron 15:909–918). Additional factors include the size of the patient, the age of the patient, the general condition of the patient, the particular disease being treated, the severity of the disease, the presence of other drugs in the patient, the in vivo activity of the adenosine agonist, and the like. The trial dosages would be chosen after consideration of the results of animal studies and the clinical literature. It will be appreciated by the person of ordinary skill in the art that information such as binding constants and Ki derived from in vitro adenosine receptor binding competition assays may also be used in calculating dosages.

A typical human dose of the compound adenosine released locally over an extended period would be from about 1 to 500 ng released per day, preferably from about 5 to 100 ng released per day, and most preferably about 10 to 50 ng released per day. For adenosine analogs and adenosine receptor agonists containing a different Ki for the adenosine receptor, these values would of course be altered accordingly.

Accordingly, adenosine-releasing cells or polymers are administered to subjects so as to reduce or ameliorate symptoms associated with epilepsy or chronic pain. Therapeutic endpoints for the treatment of epilepsy include a reduction of disease parameters such as seizure frequency, seizure severity and EEG-abnormalities. Effectiveness of pain syndrome treatment is assessed by (1) an improvement, as measured by subjective pain rating scales, in pain severity, pain quality and pain threshold; and/or (2) normalization or reduction of pain-induced increases in blood hormone levels.

For use in inhibiting pain syndromes or epilepsy in a subject, the present invention also provides in one of its aspects a kit or package, in the form of a sterile-filled vial or ampoule, that contains adenosine or an adenosine-releasing cell. In one embodiment, the kit contains an adenosine-releasing polymer, as an administration-ready formulation, in either unit dose or multi-dose amounts, wherein the package incorporates a label instructing use of its contents for the treatment of epilepsy or pain syndromes. Alternatively, and according to another embodiment of the invention, the package provides adenosine and unpolymerized monomer carrier in a form, such as a lyophilized form, suitable for reconstitution and polymerization in a suitable carrier, such as phosphate-buffered saline, to form an adenosine-releasing polymer.

In another embodiment, the package is a sterile-filled vial or ampoule containing an adenosine-releasing cell or cell line. For storage and transport, the adenosine-releasing cell or cell line should be frozen. Preferably, the package also contains an cell encapsidation agent, and instructions for its use. Optionally, the package may also contain media and reagents for culturing the adenosine-releasing cell or cell line, and for forming an encapsidated cell implant. In yet another embodiment, the package is a sterile encapsidated adenosine-releasing cell implant.

The invention having been described, the following examples are offered by way of illustration and not limitation.

6. EXAMPLES

6.1. Cells Bioengineered to release adenosine

Generation of immortalized adenosine-releasing cells from adenosine deaminase knock-out mice was done as follows.

a) Mouse Breeding:

Heterozygous adenosine deaminase knock-out mice ADA (−/+) (Wakamiya et al., 1995), commercially available from the Jackson Labs, Bar Harbor, Maine, USA, have been bred in our Institute to Immortomice™ (tsA58 (−/−)) (Jat et al., 1991) which are purchased from the Charles River Laboratories, UK. In this way a new mouse line called ADA-Immortomouse ADA (+/−) tsA58 (+/+) was generated.

b) Derivation of conditionally immortalized fibroblasts:

ADA (+/−) tsA58 (+/+) mice were bred to ADA (+/−) tsA58 (−/−) mice. From pregnant females, embryos were isolated at embryonic day 14 under sterile conditions and processed individually. Head, intestine, heart, liver, lung and spleen were removed and frozen for later PCR analysis to determine those embryos having an ADA (−/−) tsA58 (+/−) genotype.

To genotype the cell lines, 3 different PCR reactions with allele-specific primers were performed using DNA isolated from the frozen tissues via standard procedures. The ADA knock-out specific primers (for diagnosis of ADA (+/−) and ADA (−/−) mice) were primers pGK and ExVI-A.

Primer pGK:

5'-ATG CTC CAG ACT GCC TTG GGA AAA GC-3' (SEQ ID NO:1) is specific for the PGK promoter of the neomycine resistance gene cassette used for the knock-out allele;

Primer EXVI-A:

5'-TAC ACA GCT CCA ACA CCT CAA GGG AC-3' (SEQ ID NO:2) is specific for the adenosine deaminase gene.

The primers used for detecting the presence of the ADA wild type gene (ADA(+/−) and ADA(+/+) mice) were primer ExVI-A (SEQ ID NO:2) as above, and primer EXV-S:

5'-AAA GTC CTC CCT CTT CCT CTC TCC AC-3' (SEQ ID NO:3), which is specific for the adenosine deaminase gene.

The presence of the tsA58 allele was determined using primers SV40S and Sv4OA.

SV40S: 5'-CTC CTA GCT CAA AGT TCA GCC TGT CC-3' (SEQ ID NO:4)

Sv4OA: 5'-ACT CCA CAC AGG CAT AGA GTG TCT GC-3' (SEQ ID NO:5)

PCR reactions were performed in a total volume of 50 µl consisting of 32.75 µl H$_2$O, 1 µl DNA (300 to 600 ng), 5 µl 10×PCR buffer (166 mM ammonium sulphate, 670 mM Tris-HCl pH 8.8, 67 mM MgCl$_2$, 50 mM 2-mercaptoethanol, 67 µM EDTA), 0.4 µl 1% gelatine, 5 µl DMSO, 5 µl 10 mM dNTP mix, 0.6 µl 10 µM primer mix (containing the two appropriate diagnostic primers in a concentration of 10 µM each) and 0.25 µM Taq polymerase (5 U/µl; GIBCO/BRL). The reaction conditions were an initial denaturation of 2 minutes at 94° C., followed by 40 cycles of denaturation at 93° C. for 30 seconds; annealing at 55° C. for 30 seconds, and extension at 65° C. for 2 minutes.

The remnant tissue from ADA (−/−) tsA58 (+/−) embryos was used to harvest conditionally immortalized fibroblasts as follows. Tissue was cut, washed with DMEM-medium (Gibco/BRL) and centrifuged for 5 minutes at 1000 rpm. The sediments were incubated for 10 minutes in 2 ml of PBS containing 0.1% (w/v) trypsin (GIBCO/BRL, Basel, CH) and 1 mM EDTA at room temperature, then passaged approximately 20 times through a Pasteur pipette until a fine suspension resulted. This suspension was centrifuged for 5 min at 1000 rpm and the resulting sediment of cells (approx. 10$^7$ cells) resuspended in 5 ml complete medium (DMEM, 2mM glutamine, 10% FCS, 100 U/ml Pen/Strep, +10 U/ml recombinant mouse gamma-interferon; all products from Gibco/BRL Life Technologies). This suspension was kept for 5 min to allow sedimentation of large clumps of cells or tissue. The supernatant was then seeded on two 90 mm culture dishes and incubated with 10 ml complete medium at 33° C. at 5% $CO_2$. Under these conditions the cells are immortalized at 33° C. and can be passaged indefinitely (in this experiment, cells were passaged for more than 60 passages until further passaging was halted).

The division rate of ADA-Immortofibroblasts (ADA(−/−) tsA58 (+/−) is 10 to 12 divisions per week. In routine culturing, cells are passaged two times a week at a ratio of 1:5 to 1:6. After changing the culture conditions (i.e. without gamma-interferon and at 37° C.) the cells stop dividing and secrete 40 to 600 ng adenosine /$10^6$ cells/day.

These cells were also tested for whether, in addition to adenosine, they might also release toxic agents of unknown composition. For this purpose, primary neuronal cultures of cerebellar granule cells were grown in medium conditioned by ADA-immorto-fibroblasts. over nine days of culturing, no toxic effects were observed in the neurons.

6.2. Construction of adenosine-releasing cell capsule

Bioengineered fibroblasts with a high release rate of adenosine (ADA-Immorto-Fibroblasts, Example 6.1.1) were prepared as described above. These cells were encapsulated, in collaboration with the groups of P. Aebischer (Lausanne, Switzerland) into a polymer hollow fiber capsule according to the method of Aebischer et al., 1991, Exp. Neurol. 111, 269–275; and Tai and Sun, 1993, FASEB J. 7, 1061–1069. The capsules were composed of a 60:40 polyacrylnitrile :polyvinylchloride copolymer (PAN/PVC) (Aebischer et al., 1991) and contained $2 \times 10^5$ cells (FIG. 1). One capsule was found to release 230 pmol adenosine per day.

6.3. Therapeutic effectiveness of locally released adenosine from a cell capsule in an animal model of epilepsy Cell capsules pre pared as described above in Example 6.2 were grafted into the lateral brain ventricle of fully kindled rats (1 capsule per rat). Prior to grafting, rats responded to every test stimulation with grade 5 seizures and a strong afterdischarge as shown by EEG recordings (FIG. 2, top). After grafting capsules containing adenosine-releasing cells, seizures were completely suppressed. This suppression is demonstrated by the lack of any form of afterdischarge in the respective EEG-recordings (FIG. 2, bottom). Suppression of epileptic discharge was maintained for at least 2 weeks following implantation (FIG. 3). The recording presented in the bottom part of the figure is representative and was taken 14 days after implantation.

In control animals, capsules containing fibroblasts of genotype ADA (+/+), tsA58 (+/−) (no release of adenosine) were grafted. These animals showed no protection against seizure activity.

It is noteworthy that rats containing adenosine-releasing implants did not show any overt behavioral deficits. In particular, there were no signs of sedation, which is a prominent side effect after systemic administration of adenosine.

6.4 Construction of adenosine-releasing polymer

As a non-cellular device, polymers can be used as a vehicle for the delivery of adenosine or structurally related compounds. This strategy was followed to construct a biocompatible polymer generated from ethylene vinyl acetate dissolved in methylene chloride (10% w/v) according to the method of Winn et al., 1989, Exp. Neurol. 105, 244–250. Adenosine added at the monomer stage was integrated into the polymer and subsequently released by diffusion. From a single polymer (1 mm long, 0.5 mm diameter, 0.15 mg) containing 20% of adenosine (w/v), the release of adenosine into 100 µl Ringer's solution in vitro followed a logarithmically decreasing kinetic at an initial rate of 240 ng adenosine per day, as detected by an HPLC-detection assay. After the first 24 hours, an adenosine concentration of 9.0 µM is reached in the test volume. After one week the release went down to 24 ng adenosine per day and after 14 days the release of adenosine from the polymer had expired.

6.5. Therapeutic effectiveness of locally released adenosine from a polymer in an animal model of epilepsy Polymers made of ethylene vinyl acetate in methylene chloride (10% w/v) containing adenosine were prepared according to Winn et al., 1989, supra, and implanted into the ventricle of fully kindled rats. The polymers initially released adenosine in concentrations of 1–10 µM.

Following the unilateral implantation of adenosine-releasing polymers into a brain ventricle of fully kindled rats (grade 5), the animals showed a profound reduction by 75% of epileptic convulsions/seizures (FIG. 3). EEG analysis demonstrated that the average duration of the afterdischarge of 44.5 s in fully kindled rats (measured after the test stimulation) was reduced to a value of 23 s. At 2 weeks after implantation, the protective effect of the polymers had expired. The animals developed seizures and convulsions representing the kindled state before polymer implantation (FIG. 3). The loss of effectiveness is due to the lack of adenosine remaining in the polymer after a period of 2 weeks. The duration of the afterdischarge was restored to values (46.5 s) representing the kindled state before polymer implantation. Control animals which received bovine serum albumin (BSA)-releasing polymers, or animals which were sham-operated, did not show any protection against seizures (data ot shown).

6.6. Therapeutic effectiveness of locally released adenosine in an animal model of chronic pain syndrome Effects on amelioration of pain syndromes are tested in our different animal models: (1) hot plate; (2) tail-flick; (3) formalin test; and (4) nerve ligation. In all cases, denosine is applied locally (released from an adenosine-releasing polymer or from encapsidated adenosine-releasing cells) to the spinal cord by intrathecal or epidural implantation. The antinociceptive activity is assessed by standard parameters. In the hot plate test, the time required for the animal to lick its paws is measured. In the tail-flick test, the time between application of a heat stimulus and the tail-flick reaction is assessed. In the formalin-test, the use of the injected paw in locomotion is determined relative to the uninjected paw. In the nerve ligation test (sciatic nerve), the skin temperature and withdrawal of the hindpaw is measured. Local, chronic release of adenosine exhibits antinociceptive activity.

EQUIVALENTS

The foregoing written specification is sufficient to enable one skilled in the art to practice the invention. Indeed, various modifications of the above-described means for carrying out the invention which are obvious to those skilled in the field of molecular biology, medicine or related fields are intended to be within the scope of the following claims.

What is claimed is:

1. A method of inhibiting neuronal activity leading to a focal epileptic seizure in a patient, the method comprising delivering an effective amount of a continuous local dose of adenosine into the brain of a patient in need thereof, and wherein the continuous local dose of adenosine is delivered by implanting encapsidated adenosine-releasing cells.

2. The method of claim 1, wherein the adenosine-releasing cells are not derived from the cells of the patient.

3. The method of claim 1, wherein the patient has temporal lobe epilepsy, and wherein the adenosine-releasing cells are implanted into or near the epileptogenic focus.

4. A method of treating focal epilepsy in a patient, the method comprising delivering an effective amount of a continuous local dose of adenosine to the brain of a patient in need thereof, thereby reducing epileptic activity in the patient, and wherein the continuous local dose of adenosine is delivered by implanting encapsidated adenosine-releasing cells in the brain of the patient.

5. The method of claim 4, wherein the adenosine-releasing cells are not derived from the cells of the patient.

6. The method of claim 4, wherein the adenosine-releasing cells are derived from a subject with severe combined immunodeficiency disease (SCID).

7. The method of claim 4, wherein the patient suffers from temporal lobe epilepsy, and wherein the adenosine-releasing cells are implanted into or near the epileptogenic focus.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:1:

ATGCTCCAGA CTGCCTTGGG AAAAGC                           26

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:2:

TACACAGCTC CAACACCTCA AGGGAC                           26

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:3:

AAAGTCCTCC CTCTTCCTCT CTCCAC                           26

(2) INFORMATION FOR SEQ ID NO:4:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:4:

CTCCTAGCTC AAAGTTCAGC CTGTCC                           26

(2) INFORMATION FOR SEQ ID NO:5:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:5:

ACTCCACACA GGCATAGAGT GTCTGC                           26